(12) United States Patent
Coroneo

(10) Patent No.: US 10,226,380 B2
(45) Date of Patent: *Mar. 12, 2019

(54) OCULAR PRESSURE REGULATION

(71) Applicant: Novartis AG, Basel (CH)

(72) Inventor: Minas Theodore Coroneo, Menlo Park, CA (US)

(73) Assignee: Novartis AG, Basel (CH)

(*) Notice: Subject to any disclaimer, the term of this patent is extended or adjusted under 35 U.S.C. 154(b) by 349 days.

This patent is subject to a terminal disclaimer.

(21) Appl. No.: 15/165,759

(22) Filed: May 26, 2016

(65) Prior Publication Data

US 2016/0346125 A1    Dec. 1, 2016

Related U.S. Application Data

(63) Continuation of application No. 14/199,737, filed on Mar. 6, 2014, now Pat. No. 9,351,873, which is a continuation of application No. 12/905,003, filed on Oct. 14, 2010, now Pat. No. 8,808,220, which is a continuation of application No. 11/615,642, filed on Dec. 22, 2006, now Pat. No. 8,128,588, which is a continuation of application No. 10/712,277, filed on Nov. 14, 2003, now Pat. No. 7,291,125.

(51) Int. Cl.
*A61M 5/00* (2006.01)
*A61F 9/007* (2006.01)
*A61F 2/14* (2006.01)

(52) U.S. Cl.
CPC .......... *A61F 9/00781* (2013.01); *A61F 2/148* (2013.01)

(58) Field of Classification Search
CPC ................................... A61F 9/00781

USPC ......... 604/8, 9, 264; 623/4.1, 6.12; 606/107, 606/108

See application file for complete search history.

(56) References Cited

U.S. PATENT DOCUMENTS 2,990,670 A    7/1961    Kingsbury
3,439,675 A    4/1969    Cohen
(Continued)

FOREIGN PATENT DOCUMENTS

CN    1225027 A    8/1999
CN    1285724 A    2/2001
(Continued)

OTHER PUBLICATIONS

Barsky et al. "Evaluation of absorbable gelatin film (Gelfilm) in cyclodialysis clefts" Arch. Ophth. 60(6): 1044/1052,1958.
(Continued)

*Primary Examiner* — Leslie Deak
(74) *Attorney, Agent, or Firm* — Mintz Levin Cohn Ferris Glovsky and Popeo, P.C.

(57) ABSTRACT

Disclosed are devices and methods of treating an ocular disorder including forming a self-sealing incision in a cornea into an anterior chamber of an eye; introducing through the incision a fluid drainage tube having a distal end, a proximal end and a longitudinal, internal lumen extending through the fluid drainage tube, wherein at least the proximal end passes through the anterior chamber; and implanting the distal end of the fluid drainage tube in fluid communication with the suprachoroidal space such that the proximal end of the fluid drainage tube remains in fluid communication with the anterior chamber.

16 Claims, 4 Drawing Sheets

(56) References Cited

U.S. PATENT DOCUMENTS

| | | |
|---|---|---|
| 3,767,759 A | 10/1973 | Wichterle |
| 3,788,327 A | 1/1974 | Donowitz et al. |
| 3,915,172 A | 10/1975 | Wichterle et al. |
| 4,037,604 A | 7/1977 | Newkirk |
| 4,402,681 A | 9/1983 | Haas et al. |
| 4,457,757 A | 7/1984 | Molteno |
| 4,521,210 A | 6/1985 | Wong |
| 4,554,918 A | 11/1985 | White |
| 4,604,087 A | 8/1986 | Joseph |
| 4,617,715 A | 10/1986 | Koistinen et al. |
| 4,634,418 A | 1/1987 | Binder |
| 4,722,724 A | 2/1988 | Schocket |
| 4,750,901 A | 6/1988 | Molteno |
| 4,787,885 A | 11/1988 | Binder |
| 4,826,478 A | 5/1989 | Schocket |
| 4,846,172 A | 7/1989 | Berlin |
| 4,863,457 A | 9/1989 | Lee |
| 4,886,488 A | 12/1989 | White |
| 4,900,300 A | 2/1990 | Lee |
| 4,946,436 A | 8/1990 | Smith |
| 4,968,296 A | 11/1990 | Ritch et al. |
| 5,041,081 A | 8/1991 | Odrich |
| 5,071,408 A | 12/1991 | Ahmed |
| 5,073,163 A | 12/1991 | Lippman |
| 5,092,837 A | 3/1992 | Ritch et al. |
| 5,127,901 A | 7/1992 | Odrich |
| 5,171,213 A | 12/1992 | Price, Jr. |
| 5,178,604 A | 1/1993 | Baerveldt et al. |
| 5,180,362 A | 1/1993 | Worst |
| 5,284,476 A | 2/1994 | Koch |
| 5,300,020 A | 4/1994 | L'Esperance, Jr. |
| 5,338,291 A | 8/1994 | Speckman et al. |
| 5,342,370 A | 8/1994 | Simon et al. |
| 5,346,464 A | 9/1994 | Camras |
| 5,370,607 A | 12/1994 | Memmen |
| 5,372,577 A | 12/1994 | Ungerleider |
| 5,397,300 A | 3/1995 | Baerveldt et al. |
| 5,423,777 A | 6/1995 | Tajiri et al. |
| 5,433,701 A | 7/1995 | Rubinstein |
| 5,443,505 A | 8/1995 | Wong et al. |
| 5,454,746 A | 10/1995 | Guegan et al. |
| 5,476,445 A | 12/1995 | Baerveldt et al. |
| 5,558,629 A | 9/1996 | Baerveldt et al. |
| 5,558,630 A | 9/1996 | Fisher |
| 5,569,197 A | 10/1996 | Helmus et al. |
| RE35,390 E | 12/1996 | Smith |
| 5,601,094 A | 2/1997 | Reiss |
| 5,626,558 A | 5/1997 | Suson |
| 5,626,559 A | 5/1997 | Solomon |
| 5,651,782 A | 7/1997 | Simon et al. |
| 5,676,944 A | 10/1997 | Alvarado et al. |
| 5,702,414 A | 12/1997 | Richter et al. |
| 5,704,907 A | 1/1998 | Nordquist et al. |
| 5,713,844 A | 2/1998 | Peyman |
| 5,741,292 A | 4/1998 | Mendius |
| 5,743,868 A | 4/1998 | Brown et al. |
| 5,749,879 A | 5/1998 | Middleman et al. |
| 5,752,928 A | 5/1998 | de Roulhac et al. |
| 5,792,075 A | 8/1998 | Schwager |
| 5,807,244 A | 9/1998 | Barot |
| 5,807,302 A | 9/1998 | Wandel |
| 5,868,697 A | 2/1999 | Richter et al. |
| 5,882,327 A | 3/1999 | Jacob |
| 5,893,837 A | 4/1999 | Eagles et al. |
| 5,941,250 A | 8/1999 | Aramant et al. |
| 5,968,058 A | 10/1999 | Richter et al. |
| 6,007,510 A | 12/1999 | Nigam |
| 6,007,511 A | 12/1999 | Prywes |
| 6,019,786 A | 2/2000 | Thompson |
| 6,036,678 A | 3/2000 | Giungo |
| 6,050,970 A | 4/2000 | Baerveldt |
| 6,050,999 A | 4/2000 | Paraschac et al. |
| 6,077,299 A | 6/2000 | Adelberg et al. |
| 6,102,045 A | 8/2000 | Nordquist et al. |
| 6,142,969 A | 11/2000 | Nigam |
| 6,152,918 A | 11/2000 | Padilla et al. |
| 6,174,307 B1 | 1/2001 | Daniel et al. |
| 6,186,974 B1 | 2/2001 | Allan et al. |
| 6,203,513 B1 | 3/2001 | Yaron et al. |
| 6,221,078 B1 | 4/2001 | Bylsma |
| 6,251,090 B1 | 6/2001 | Avery et al. |
| 6,261,256 B1 | 7/2001 | Ahmed |
| 6,264,668 B1 | 7/2001 | Prywes |
| 6,270,472 B1 | 8/2001 | Antaki et al. |
| 6,331,313 B1 | 12/2001 | Wong et al. |
| 6,375,642 B1 | 4/2002 | Grieshaber et al. |
| 6,383,219 B1 | 5/2002 | Telandro et al. |
| 6,450,984 B1 | 9/2002 | Lynch et al. |
| 6,464,724 B1 | 10/2002 | Lynch et al. |
| 6,468,283 B1 | 10/2002 | Richter et al. |
| 6,471,666 B1 | 10/2002 | Odrich |
| 6,471,777 B1 | 10/2002 | Kobayashi et al. |
| 6,494,857 B1 | 12/2002 | Neuhann |
| 6,508,779 B1 | 1/2003 | Suson |
| 6,510,600 B2 | 1/2003 | Yaron et al. |
| 6,524,275 B1 | 2/2003 | Lynch et al. |
| 6,533,768 B1 | 3/2003 | Hill |
| 6,537,568 B2 | 3/2003 | Olejnik et al. |
| 6,544,208 B2 | 4/2003 | Ethier et al. |
| 6,544,249 B1 | 4/2003 | Yu et al. |
| 6,558,342 B1 | 5/2003 | Yaron et al. |
| 6,561,974 B1 | 5/2003 | Grieshaber et al. |
| 6,579,256 B2 | 6/2003 | Hughes |
| 6,589,203 B1 | 7/2003 | Mitrev |
| 6,595,945 B2 | 7/2003 | Brown |
| 6,626,858 B2 | 9/2003 | Lynch et al. |
| 6,638,239 B1 | 10/2003 | Bergheim et al. |
| 6,648,283 B2 | 11/2003 | Chase et al. |
| 6,666,841 B2 | 12/2003 | Gharib et al. |
| 6,676,607 B2 | 1/2004 | de Juan, Jr. et al. |
| 6,699,210 B2 | 3/2004 | Williams et al. |
| 6,699,211 B2 | 3/2004 | Savage |
| 6,719,750 B2 | 4/2004 | Varner et al. |
| 6,726,664 B2 | 4/2004 | Yaron et al. |
| 6,726,676 B2 | 4/2004 | Stegmann et al. |
| 6,730,056 B1 | 5/2004 | Ghaem et al. |
| 6,736,791 B1 | 5/2004 | Tu et al. |
| 6,741,666 B1 | 5/2004 | Henry et al. |
| 6,752,753 B1 | 6/2004 | Hoskins et al. |
| 6,780,164 B2 | 8/2004 | Bergheim et al. |
| 6,783,544 B2 | 8/2004 | Lynch et al. |
| 6,786,888 B1 | 9/2004 | Zadno-Azizi et al. |
| 6,827,699 B2 | 12/2004 | Lynch et al. |
| 6,827,700 B2 | 12/2004 | Lynch et al. |
| 6,881,197 B1 | 4/2005 | Nigam |
| 6,881,198 B2 | 4/2005 | Brown |
| 6,939,298 B2 | 9/2005 | Brown et al. |
| 6,955,656 B2 | 10/2005 | Bergheim et al. |
| 6,962,573 B1 | 11/2005 | Wilcox |
| 6,966,888 B2 | 11/2005 | Cullen et al. |
| 6,969,384 B2 | 11/2005 | de Juan, Jr. et al. |
| 6,981,958 B1 | 1/2006 | Gharib et al. |
| 6,989,007 B2 | 1/2006 | Shadduck |
| 7,041,077 B2 | 5/2006 | Shields |
| 7,090,681 B2 | 8/2006 | Weber et al. |
| 7,094,225 B2 | 8/2006 | Tu et al. |
| 7,135,009 B2 | 11/2006 | Tu et al. |
| 7,160,264 B2 | 1/2007 | Lisk, Jr. et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,195,774 B2 | 3/2007 | Carvalho et al. |
| 7,207,965 B2 | 4/2007 | Simon |
| 7,220,238 B2 | 5/2007 | Lynch et al. |
| 7,273,475 B2 | 9/2007 | Tu et al. |
| 7,291,125 B2 | 11/2007 | Coroneo |
| 7,297,130 B2 | 11/2007 | Bergheim et al. |
| 7,331,984 B2 | 2/2008 | Tu et al. |
| 7,431,710 B2 | 10/2008 | Tu et al. |
| 7,488,303 B1 | 2/2009 | Haffner et al. |
| 7,563,241 B2 | 7/2009 | Tu et al. |
| 7,850,637 B2 | 12/2010 | Lynch et al. |
| 7,850,638 B2 * | 12/2010 | Coroneo .................. A61F 2/148 604/8 |

(56) References Cited

U.S. PATENT DOCUMENTS

| | | | |
|---|---|---|---|
| 7,857,782 B2 | 12/2010 | Tu et al. | |
| 7,972,616 B2 | 7/2011 | Dubrow et al. | |
| 8,075,511 B2 | 12/2011 | Tu et al. | |
| 8,128,588 B2 | 3/2012 | Coroneo | |
| 8,702,727 B1 | 4/2014 | Harrington et al. | |
| 8,771,218 B2 * | 7/2014 | Coroneo | A61F 2/148 604/8 |
| 2001/0000527 A1 | 4/2001 | Yaron et al. | |
| 2001/0025150 A1 | 9/2001 | de Juan et al. | |
| 2002/0013546 A1 | 1/2002 | Grieshaber et al. | |
| 2002/0013572 A1 | 1/2002 | Berlin | |
| 2002/0026200 A1 | 2/2002 | Savage | |
| 2002/0072673 A1 | 6/2002 | Yamamoto et al. | |
| 2002/0087111 A1 | 7/2002 | Ethier et al. | |
| 2002/0111608 A1 | 8/2002 | Baerveldt et al. | |
| 2002/0128613 A1 | 9/2002 | Nakayama | |
| 2002/0133168 A1 | 9/2002 | Smedley et al. | |
| 2002/0143284 A1 | 10/2002 | Tu et al. | |
| 2002/0156413 A1 | 10/2002 | Williams et al. | |
| 2002/0165478 A1 | 11/2002 | Gharib et al. | |
| 2002/0169130 A1 | 11/2002 | Tu et al. | |
| 2002/0169468 A1 | 11/2002 | Brown | |
| 2002/0177856 A1 | 11/2002 | Richter et al. | |
| 2002/0188308 A1 | 12/2002 | Tu et al. | |
| 2002/0193725 A1 | 12/2002 | Odrich | |
| 2002/0193804 A1 | 12/2002 | Tickle | |
| 2003/0009124 A1 | 1/2003 | Lynch et al. | |
| 2003/0028127 A1 | 2/2003 | Balzum et al. | |
| 2003/0028228 A1 | 2/2003 | Sand | |
| 2003/0055372 A1 | 3/2003 | Lynch et al. | |
| 2003/0060752 A1 | 3/2003 | Bergheim et al. | |
| 2003/0069637 A1 | 4/2003 | Lynch et al. | |
| 2003/0088260 A1 | 5/2003 | Smedley et al. | |
| 2003/0097151 A1 | 5/2003 | Smedley et al. | |
| 2003/0097171 A1 | 5/2003 | Elliott | |
| 2003/0109883 A1 | 6/2003 | Matsuzaki et al. | |
| 2003/0120200 A1 | 6/2003 | Bergheim et al. | |
| 2003/0135149 A1 | 7/2003 | Cullen et al. | |
| 2003/0139809 A1 | 7/2003 | Worst et al. | |
| 2003/0181848 A1 | 9/2003 | Bergheim et al. | |
| 2003/0187384 A1 | 10/2003 | Bergheim et al. | |
| 2003/0187385 A1 | 10/2003 | Bergheim et al. | |
| 2003/0191428 A1 | 10/2003 | Bergheim et al. | |
| 2003/0208163 A1 | 11/2003 | Yaron et al. | |
| 2003/0220602 A1 | 11/2003 | Lynch et al. | |
| 2003/0220603 A1 | 11/2003 | Lynch et al. | |
| 2003/0229303 A1 | 12/2003 | Haffner et al. | |
| 2003/0232015 A1 | 12/2003 | Brown et al. | |
| 2003/0236483 A1 | 12/2003 | Ren | |
| 2003/0236484 A1 | 12/2003 | Lynch et al. | |
| 2004/0015140 A1 | 1/2004 | Shields | |
| 2004/0024345 A1 | 2/2004 | Gharib et al. | |
| 2004/0050392 A1 | 3/2004 | Tu et al. | |
| 2004/0073156 A1 | 4/2004 | Brown | |
| 2004/0088048 A1 | 5/2004 | Richter et al. | |
| 2004/0092856 A1 | 5/2004 | Dahan | |
| 2004/0097984 A1 | 5/2004 | Zapata | |
| 2004/0102729 A1 | 5/2004 | Haffner et al. | |
| 2004/0111050 A1 | 6/2004 | Smedley et al. | |
| 2004/0127843 A1 | 7/2004 | Tu et al. | |
| 2004/0147870 A1 | 7/2004 | Burns et al. | |
| 2004/0148022 A1 | 7/2004 | Eggleston | |
| 2004/0193095 A1 | 9/2004 | Shadduck | |
| 2004/0193262 A1 | 9/2004 | Shadduck | |
| 2004/0210181 A1 | 10/2004 | Vass et al. | |
| 2004/0210185 A1 | 10/2004 | Tu et al. | |
| 2004/0216749 A1 | 11/2004 | Tu | |
| 2004/0225250 A1 | 11/2004 | Yablonski | |
| 2004/0236343 A1 | 11/2004 | Taylor et al. | |
| 2004/0249333 A1 | 12/2004 | Bergheim et al. | |
| 2004/0254517 A1 | 12/2004 | Quiroz-Mercado et al. | |
| 2004/0254519 A1 | 12/2004 | Tu et al. | |
| 2004/0254520 A1 | 12/2004 | Porteous et al. | |
| 2004/0254521 A1 | 12/2004 | Simon | |
| 2004/0260227 A1 | 12/2004 | Lisk et al. | |
| 2004/0260228 A1 | 12/2004 | Lynch et al. | |
| 2005/0008673 A1 | 1/2005 | Snyder et al. | |
| 2005/0038334 A1 | 2/2005 | Lynch et al. | |
| 2005/0049578 A1 | 3/2005 | Tu et al. | |
| 2005/0085892 A1 | 4/2005 | Goto et al. | |
| 2005/0090806 A1 | 4/2005 | Lynch et al. | |
| 2005/0090807 A1 | 4/2005 | Lynch et al. | |
| 2005/0101967 A1 | 5/2005 | Weber et al. | |
| 2005/0107734 A1 | 5/2005 | Coroneo | |
| 2005/0119601 A9 | 6/2005 | Lynch et al. | |
| 2005/0119636 A1 | 6/2005 | Haffner et al. | |
| 2005/0119737 A1 | 6/2005 | Bene et al. | |
| 2005/0125003 A1 | 6/2005 | Pinchuk et al. | |
| 2005/0143817 A1 | 6/2005 | Hunter et al. | |
| 2005/0149080 A1 | 7/2005 | Hunter et al. | |
| 2005/0175663 A1 | 8/2005 | Hunter et al. | |
| 2005/0181011 A1 | 8/2005 | Hunter et al. | |
| 2005/0181977 A1 | 8/2005 | Hunter et al. | |
| 2005/0182350 A1 | 8/2005 | Nigam | |
| 2005/0191331 A1 | 9/2005 | Hunter et al. | |
| 2005/0192527 A1 | 9/2005 | Gharib et al. | |
| 2005/0197613 A1 | 9/2005 | Sniegowski et al. | |
| 2005/0209549 A1 | 9/2005 | Bergheim et al. | |
| 2005/0209550 A1 | 9/2005 | Bergheim et al. | |
| 2005/0232972 A1 | 10/2005 | Odrich | |
| 2005/0244462 A1 | 11/2005 | Farooq | |
| 2005/0250788 A1 | 11/2005 | Tu et al. | |
| 2005/0266047 A1 | 12/2005 | Tu et al. | |
| 2005/0267397 A1 | 12/2005 | Bhalla | |
| 2005/0267398 A1 | 12/2005 | Protopsaltis et al. | |
| 2005/0271704 A1 | 12/2005 | Tu et al. | |
| 2005/0273033 A1 | 12/2005 | Grahn et al. | |
| 2005/0277864 A1 | 12/2005 | Haffner et al. | |
| 2005/0283108 A1 | 12/2005 | Savage | |
| 2005/0288617 A1 | 12/2005 | Yaron et al. | |
| 2005/0288619 A1 | 12/2005 | Gharib et al. | |
| 2006/0004348 A1 | 1/2006 | Scheller et al. | |
| 2006/0020248 A1 | 1/2006 | Prescott | |
| 2006/0032507 A1 | 2/2006 | Tu | |
| 2006/0036207 A1 | 2/2006 | Koonmen et al. | |
| 2006/0047263 A1 | 3/2006 | Tu et al. | |
| 2006/0069340 A1 | 3/2006 | Simon | |
| 2006/0074375 A1 | 4/2006 | Bergheim et al. | |
| 2006/0084907 A1 | 4/2006 | Bergheim et al. | |
| 2006/0116626 A1 | 6/2006 | Smedley et al. | |
| 2006/0149194 A1 | 7/2006 | Conston et al. | |
| 2006/0155238 A1 | 7/2006 | Shields | |
| 2006/0173397 A1 | 8/2006 | Tu et al. | |
| 2006/0195055 A1 | 8/2006 | Bergheim et al. | |
| 2006/0195056 A1 | 8/2006 | Bergheim et al. | |
| 2006/0200113 A1 | 9/2006 | Haffner et al. | |
| 2006/0235367 A1 | 10/2006 | Takashima et al. | |
| 2006/0241580 A1 | 10/2006 | Mittelstein et al. | |
| 2006/0241749 A1 | 10/2006 | Tu et al. | |
| 2006/0276739 A1 | 12/2006 | Brown | |
| 2007/0010827 A1 | 1/2007 | Tu et al. | |
| 2007/0088424 A1 | 4/2007 | Greenberg et al. | |
| 2007/0088432 A1 | 4/2007 | Solovay et al. | |
| 2007/0112292 A1 | 5/2007 | Tu et al. | |
| 2007/0118147 A1 | 5/2007 | Smedley et al. | |
| 2007/0191863 A1 | 8/2007 | De Juan et al. | |
| 2007/0276315 A1 | 11/2007 | Haffner et al. | |
| 2007/0276316 A1 | 11/2007 | Haffner et al. | |
| 2007/0282244 A1 | 12/2007 | Tu et al. | |
| 2007/0282245 A1 | 12/2007 | Tu et al. | |
| 2007/0293807 A1 | 12/2007 | Lynch et al. | |
| 2008/0015488 A1 | 1/2008 | Tu et al. | |
| 2008/0045878 A1 | 2/2008 | Bergheim et al. | |
| 2008/0108933 A1 | 5/2008 | Yu et al. | |
| 2008/0200860 A1 | 8/2008 | Tu et al. | |
| 2008/0228127 A1 | 9/2008 | Burns et al. | |
| 2008/0234624 A2 | 9/2008 | Bergheim et al. | |
| 2009/0036819 A1 | 2/2009 | Tu et al. | |
| 2009/0036840 A1 | 2/2009 | Viray et al. | |
| 2010/0010416 A1 | 1/2010 | Juan, Jr. et al. | |
| 2010/0152641 A1 | 6/2010 | Yablonski | |
| 2010/0234790 A1 | 9/2010 | Tu et al. | |
| 2010/0274259 A1 | 10/2010 | Yaron et al. | |
| 2011/0028884 A1 | 2/2011 | Coroneo | |

(56) References Cited

U.S. PATENT DOCUMENTS

| | | |
|---|---|---|
| 2011/0087149 A1 | 4/2011 | Coroneo |
| 2011/0087150 A1 | 4/2011 | Coroneo |
| 2011/0087151 A1 | 4/2011 | Coroneo |
| 2012/0123316 A1 | 5/2012 | Horvath et al. |
| 2012/0220917 A1 | 8/2012 | Silvestrini et al. |
| 2013/0245532 A1 | 9/2013 | Tu |
| 2013/0281817 A1 | 10/2013 | Schaller et al. |
| 2013/0281908 A1 | 10/2013 | Schaller et al. |
| 2013/0281910 A1 | 10/2013 | Tu |
| 2014/0012279 A1 | 1/2014 | de Juan, Jr. et al. |
| 2014/0066831 A1 | 3/2014 | Silvestrini et al. |
| 2014/0081195 A1 | 3/2014 | Clauson et al. |
| 2014/0107556 A1 | 4/2014 | Silvestrini et al. |
| 2014/0135916 A1 | 5/2014 | Clauson et al. |
| 2014/0213958 A1 | 7/2014 | Clauson et al. |
| 2014/0309599 A1 | 10/2014 | Schaller |
| 2014/0323995 A1 | 10/2014 | Clauson et al. |
| 2014/0364789 A1 | 12/2014 | Schaller |
| 2014/0378886 A1 | 12/2014 | de Juan, Jr. et al. |
| 2015/0022780 A1 | 1/2015 | John et al. |
| 2015/0223982 A1 | 8/2015 | Yablonski |
| 2015/0238360 A1 | 8/2015 | de Juan, Jr. et al. |
| 2015/0320596 A1 | 11/2015 | Gifford, III et al. |
| 2015/0335487 A1 | 11/2015 | de Juan, Jr. |

FOREIGN PATENT DOCUMENTS

| | | |
|---|---|---|
| CN | 1124164 C | 10/2003 |
| CN | 1681457 A | 10/2005 |
| DE | 10042310 A1 | 3/2002 |
| EP | 0 228 185 A1 | 11/1986 |
| EP | 1184010 A2 | 3/2002 |
| EP | 1310222 A2 | 5/2003 |
| EP | 1473004 A2 | 11/2004 |
| EP | 1477146 A2 | 11/2004 |
| EP | 1418868 B1 | 3/2008 |
| EP | 1977724 A1 | 10/2008 |
| EP | 2027837 A2 | 2/2009 |
| GB | 2101891 A | 1/1983 |
| RU | 2018289 C1 | 8/1994 |
| RU | 2056818 C1 | 3/1996 |
| RU | 2074686 C1 | 3/1997 |
| RU | 2074687 C1 | 3/1997 |
| RU | 2157678 C1 | 10/2000 |
| WO | WO-89/00869 A1 | 2/1989 |
| WO | WO-91/12046 A1 | 8/1991 |
| WO | WO-92/19294 A1 | 11/1992 |
| WO | WO-94/02081 A1 | 2/1994 |
| WO | WO-94/09721 A1 | 5/1994 |
| WO | WO-94/09837 A1 | 5/1994 |
| WO | WO-94/13234 A1 | 6/1994 |
| WO | WO-95/08310 A1 | 3/1995 |
| WO | WO-96/20742 A1 | 7/1996 |
| WO | WO-96/36377 A1 | 11/1996 |
| WO | WO-98/23237 A1 | 6/1998 |
| WO | WO-98/30181 A1 | 7/1998 |
| WO | WO-99/26567 A1 | 6/1999 |
| WO | WO-00/06223 A1 | 2/2000 |
| WO | WO-00/64389 A1 | 11/2000 |
| WO | WO-00/64390 A1 | 11/2000 |
| WO | WO-00/64391 A1 | 11/2000 |
| WO | WO-00/64393 A1 | 11/2000 |
| WO | WO-00/64511 A1 | 11/2000 |
| WO | WO-01/68016 A2 | 9/2001 |
| WO | WO-01/78631 A2 | 10/2001 |
| WO | WO-01/78656 A2 | 10/2001 |
| WO | WO-01/97727 A1 | 12/2001 |
| WO | WO-02/036052 A1 | 5/2002 |
| WO | WO-02/070045 A1 | 9/2002 |
| WO | WO-02/074052 A2 | 9/2002 |
| WO | WO-02/080811 A2 | 10/2002 |
| WO | WO-02/080829 A2 | 10/2002 |
| WO | WO-02/087418 A2 | 11/2002 |
| WO | WO-02/087479 A2 | 11/2002 |
| WO | WO-02/089699 A2 | 11/2002 |
| WO | WO-02/102274 A2 | 12/2002 |
| WO | WO-03/015659 A2 | 2/2003 |
| WO | WO-03/015667 A1 | 2/2003 |
| WO | WO-03/041622 A2 | 5/2003 |
| WO | WO-03/045290 A1 | 6/2003 |
| WO | WO-03/073968 A2 | 9/2003 |
| WO | WO-03/096871 A2 | 11/2003 |
| WO | WO-03/099175 A1 | 12/2003 |
| WO | WO-2004/014218 A2 | 2/2004 |
| WO | WO-2004/026106 A2 | 4/2004 |
| WO | WO-2004/026347 A2 | 4/2004 |
| WO | WO-2004/043231 A2 | 5/2004 |
| WO | WO-2004/056294 A1 | 7/2004 |
| WO | WO-2004/060219 A1 | 7/2004 |
| WO | WO-2004/062469 A2 | 7/2004 |
| WO | WO-2004/073552 A2 | 9/2004 |
| WO | WO-2004/110391 A2 | 12/2004 |
| WO | WO-2005/016418 A1 | 2/2005 |
| WO | WO-2005/046782 A1 | 5/2005 |
| WO | WO-2005/055873 A2 | 6/2005 |
| WO | WO-2005/105197 A2 | 11/2005 |
| WO | WO-2005/107664 A2 | 11/2005 |
| WO | WO-2005/107845 A1 | 11/2005 |
| WO | WO-2006/012421 A2 | 2/2006 |
| WO | WO-2006/036715 A2 | 4/2006 |
| WO | WO-2007/087061 A2 | 8/2007 |
| WO | WO-2007/115259 A2 | 10/2007 |
| WO | WO-2007/130393 A2 | 11/2007 |
| WO | WO-2008/061043 | 5/2008 |
| WO | WO-2009/035562 A2 | 3/2009 |
| WO | WO-2012/019136 A2 | 2/2012 |

OTHER PUBLICATIONS

Bick M.W., "Use of tantalum for ocular drainage" Arch Ophthal. Oct. 1949; 42(4): 373/88.

Bietti, G., "The present state of the use of plastics in eye surgery" Acta Ophthalmol (Copenh) 1955; 33(4):337/70.

Brown et al., "Internal Sclerectomy for Glaucoma Filtering Surgery with an Automated Trephine," Archives of Ophthalmology, vol. 105, Jan. 1987.

Burchfield JC, Kass MA, Wax MB. Primary valve malfunction of the Krupin eye valve with disk. J Glaucoma. Jun. 1997;6(3):152/6.

Chiou et al. "Ultrasound biomicroscopy of eyes undergoing deep sclerectomy with collagen implant" Br J Ophthalmol 80 (1996), pp. 541-544.

Chylack LT, Bellows AR. Molecular sieving in suprachoroidal fluid formation in man. Invest Ophthalmol Vis Sci 17: 420, 1978.

Classen et al., "A histopathologic and immunohistorchemical analysis of the filtration bleb after unsuccessful glaucoma seton implantation" Am. J. Ophthalmol. 122:205/12 (1996).

Cohen et al., "First day post/operative review following uncomplicated phacoemulsification" Eye 12(4):634/6 (1998).

Collaborative Normal/Tension Study Group. Comparison of glaucomatous progression between untreated patients with normal/tension glaucoma and patients with therapeutically reduced intraocular pressures. Am J Ophthalmol 1998;126:487/97.

Coote. "Glaucoma Hollow Fiber Filters—A New Glaucoma Seton. Preliminary Results." *J. Glaucoma*. vol. 8 No. 1 Supplement (1999):p. S4.

Cullen, et al. "Anterior Chamber of Frontal Sinus Shunt for the Diversion of Aqueous Humor: A Pilot Study in Four Normal Dogs". *Veterinary Ophthalmology*. vol. 1. No. 1. (1998):31-39.

Demailly et al. "Non/penetrating deep sclerectomy (NPDS) with or without collagen device (CD) in primary open/angle glaucoma: middle/term retrospective study" International Ophthalmology 20: 131/140, 1997.

Derwent English abstract for EP 1184010, published Mar. 6, 2002 entitled: "Drainage unit for an eye, consists of a hollow line, a distribution member, and a pressure relief valve which only allows water to leave the eye chamber above a certain pressure," Accession Nbr. 12409716 [351].

Dinakaran et al., "Is the first post/operative day review necessary following uncomplicated phacoemulsification surgery?" Eye, 14(3A):364/6 (2000).

(56) References Cited

OTHER PUBLICATIONS

Draeger "Chirurgische Maβnahmen bei kongenitalem Glaukom" (Surgical Interventions in Congenital Glaucoma) Klin Monatsbl Augenheilkd 1993; 202(5): 425/427 [Article in German with English summary included].
Einmahl et al., "Evaluation of a novel biomaterial in the suprachoroidal space of the rabbit eye" Invest Ophthalmol Vis Sci. 43:1533/1539 (2002).
Ellis, RA "A Reduction of Intraocular Pressure Using Plastics in Surgery" Am J Ophth. 50; 1960, 733/742.
Emi et al., "Hydrostatic pressure of the suprachoroidal space" Invest. Ophthal. Visual Sci. 30(2):233/238 (1989).
Fanous MM, Cohn RA. Propionibacterium endophthalmitis following Molteno tube repositioning. J Glaucoma. Aug. 1997;6(4):2012.
Fuchs E., "Detachment of the choroid inadvertently during cataract surgery" [German] von Graefes Arch Ophthalmol, 51:199/224 (1900) [Article in German with English summary].
Gills et al., "Action of cyclodialysis utilizing an implant studied by manometry in a human eye" Expl Eye Res 1967; 6:75/78.
Gills JP, "Cyclodialysis implants" South Med J. 1967 60(7):692/5.
Gills, "Cyclodialysis Implants in Human Eyes" Am J Ophth 61:1966,841/846.
Goldberg "Management of Uncontrolled Glaucoma With the Molteno System" Australian and New Zealand Journal of Ophthalmology 1987; 15: 97/107.
Gordon MO, Kass. MA, for the Ocular Hypertension Treatment Study Group. The Ocular Hypertension Treatment Study. Design and baseline description of the participants. Arch Ophthalmol 1999:573/83.
Grant, W.M. , MD, Further Studies on Facility of Flow Through the Trabecular Meshwork, A.M.A. Archives of Ophthalmololgy, Oct. 1958, vol. 60, pp. 523-533.
Gross et al., "Surgical therapy of chronic glaucoma in aphakia and pseudophakia" Ophthalmology, 95:1195/201 (1988).
Harper SL, Foster CS. Intraocular lens explantation in uveitis. Int Ophthalmol Clin. 2000 Winter; 40(1):107/16.
Harrington "Cataract and glaucoma. Management of the coexistent conditions and a description of a new operation combining lens extraction with reverse cyclodialysis." Am J Ophthalmol. May 1966;61(5 Pt 2):1134/40.
Heijl A, Leske MC, Bengtsson B, et al for the Early Manifest Glaucoma Trial Group. Reduction of intraocular pressure and glaucoma progression. Results from the Early Manifest Glaucoma Trial. Arch Ophthalmol 2002;120:1268/79.
Heine I., "Cyclodialysis, a new glaucoma operation" Dtsch Med Wochenschr, 31:824/826 (1905) [Article in German with English summary included].
Hildebrand et al., "Efficacy of anterior chamber decompression in controlling early intraocular pressure spikes after uneventful phacoemulsification" J. Catact Refract Surg., 29:1087/92 (2003).
Hoskins, et al., "Aqueous Humor Outflow", Becker-Shaffer's Diagnosis and Therapy of the Glaucomas, 6th Edition, Chapter 4, pp. 41-66, 1989.
Howorth DJ, "Feasibility study for a micromachined glaucoma drainage device" Cranfield University School of industrial and manufacturing science MSc Thesis Academic Year 2001/2002 Sep. 13, 2002.
Hylton et al., "Update on prostaglandin analogs" Curr Opin Ophthalmol, 14:65/9 (2003).
In the Matter of Austrialian Patent Application No. 2006336598 in the name of Transcend Medical, Inc ("Applicant") and Opposition thereto by Glaukos Corporation ("Opponent")—Opponent's Statement of Grounds and Particulars of Opposition, dated Apr. 10, 2014.
In the Matter of Austrialian Patent Application No. 2006336598 in the name of Transcend Medical, Inc ("Applicant") and Opposition thereto by Glaukos Corporation ("Opponent")—Opponent's amended Statement of Grounds and Particulars of Opposition. (Sep. 10, 2014).
In the Matter of Austrialian Patent Application No. 2006336598 in the name of Transcend Medical, Inc ("Applicant") and Opposition thereto by Glaukos Corporation ("Opponent")—Declaration of Mr. Craig Andrews in support of Opponent's opposition. (Sep. 9, 2014).
In the Matter of Austrialian Patent Application No. 2006336598 in the name of Transcend Medical, Inc ("Applicant") and Opposition thereto by Glaukos Corporation ("Opponent")—Declaration of Dr. Ilesh Patel in support of Opponent's opposition. (Sep. 9, 2014).
In the Matter of Austrialian Patent Application No. 2006336598 in the name of Transcend Medical, Inc ("Applicant") and Opposition thereto by Glaukos Corporation ("Opponent")—Declaration of Dr. Colin Clement in support of Opponent's opposition. (Sep. 9, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Robert L. Stamper in support of Applicant's Evidence in Answer. (Dec. 4, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Jonathan G. Crowston in support of Applicant's Evidence in Answer. (Dec. 6, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Anne Jen-Wan Lee in support of Applicant's Evidence in Answer. (Dec. 7, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Colin Clement in support of Opponent's Evidence in Reply. (Feb. 8, 2015).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Ilesh Patel in support of Opponent's Evidence in Reply. (Feb. 10, 2015).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Mr. Craig Andrews in support of Opponent's Evidence in Reply. (Feb. 11, 2015).
Javitt JC, Chiang YP. Preparing for managed competition. Utilization of ambulatory eye care visits to ophthalmologists. Arch Ophthalmol 1993;111:1034/5.
Jay JL, Allan D. The benefit of early trabeculectomy versus conventional management in primary open/angle glaucoma relative to severity of disease. Eye 1989; 3:528/35.
Jordan J., "A Novel Approach to Suprachoroidal Drainage for the Surgical Treatment of Intractable Glaucoma" J. Glaucoma 2006; 15:200/205.
Karlen, M. et al., "Deep sclerectomy with collagen implant: medium term results" Br. J. Ophthalmol, Jan 1999, 83(1):6/11.
Kass MA, Heuer DK, Higginbotham EJ, et al for the Ocular Hypertension Treatment Study Group. The Ocular Hypertension Treatment Study. A randomized trial determines that topical ocular hypotensive medication delays or prevents the onset of primary open/angle glaucoma. Arch Ophthalmol 2002;120:701/13.
Klemm et al. "Die Ultraschallbiomikroskopie als Kriterium der Funktionsprüfung des suprachorioidalen Spaltes nach kammerwinkelchirurgischen Eingriffen (Ultrasound Biomicroscopic Imaging for Assessment of the Suprachoroidal Cleft after Angle Surgery)" Klinische Monatsblätter für Augenheilkunde 1997; 210: 74/77.
Klemm et al., "Experimental use of space/retaining substances with extended duration: functional and morphological results" Graefes Arch Clin Exp Ophthalmol Sep. 1995; 233(9):592/7.
Kozlov et al., "Nonpenetrating deep sclerectomy with collagen" Eye microsurgery 3:44/46 (1990) [Article in Russian with English translation included].
Krejci, L., "Cyclodialysis with hydroxymethyl methacrylate capillary strip (HCS). Animal experiments with a new approach in glaucoma drainage surgery" Ophthalmologica 1972; 164(2):113/21.

(56) References Cited

OTHER PUBLICATIONS

Krejcí L. "Microdrainage of anterior chamber of eye glaucoma operation using hydron capillary drain. " Acta Univ Carol Med Monogr. 1974;(61):1/90.
Kupfer "Studies on intraocular pressure. I. A technique for polyethylene tube implantation into the anterior chamber of the rabbit. " Arch Ophthalmol. Apr. 1961;65:565/70.
La Rocca "Gonioplasty in Glaucoma*A Preliminary Report" Br J Ophth 46:1962, 404/415.
Law et al., "Retinal Complications After Aqueous Shunt Surgical Procedures for Glaucoma" Arch Ophthal.; Dec. 1996; vol. 114:1473/1480.
Lee et al. "Aqueous-venous shunt and intraocular pressure. Preliminary report of animal studies." *Investigative Ophthalmology.* vol. 5 No. 1: 59-64. Feb. 1966.
Lee et al., "Magnetic resonance imaging of the aqueous flow in eyes implanted with the trabeculo/suprachoroidal glaucoma seton" Invest. Ophthalmol. Vis. Sci. 33:948 (1992).
Lee KY. Trabeculo/suprachoroidal shunt for treating recalcitrant and secondary glaucoma. Presented at the American Academy of Ophthalmology Annual Meeting, Anaheim, CA, 1991.
Leske MC, Heijl A, Hussein M, et al for the Early Manifest Glaucoma Trial Group. Factors for glaucoma progression and the effect of treatment. The Early Manifest Glaucoma Trial. Arch Ophthalmol 2003;121:48/56.
Lichter PR, Musch DC, Gillespie BW, et al and the CIGTS Study Group. Interim clinical outcomes in the Collaborative Initial Glaucoma Treatment Study comparing initial treatment randomized to medications or surgery. Ophthalmology 2001;108:1943/53.
Losche, W., "Proposals for improvement of cyclodialysis" Klin Monatsblatter Augenheilkd Augenarztl Fortbild 1952 121(6):715/6 [Article in German with English translation included].
Marx et al., "Use of the Ganciclovir Implant in the Treatment of Recurrent Cytomegalovirus Retinitis" Arch Ophthal.; Jul. 1996; vol. 114:815/820.
Mcpherson "Combined Trabeculotomy and Cataract Extraction as a Single Operation*" Tr. Am. Ophth. Soc., vol. LXXIV, 1976; 251/260.
Mehta KR. "The suprachoroidal hema wedge in glaucoma surgery" American Academy of Ophthalmology meeting 1977 pp. 144.
Migdal C, Gregory W, Hitchings R. Long term functional outcome after early surgery compared with laser and medicine in open/angle glaucoma. Ophthalmology 1994;101:1651/7.
Miglior S, Zeyen T, Pfeiffer N, et al for the European Glaucoma Prevention Study Group. The European Glaucoma Prevention Study design and baseline description of the participants. Ophthalmology 2002;109:1612/21.
Miki, MD et al., "Intraocular Cannula for Continuous, Chronic Drug Delivery/Histopathic Observations and Function" Arch Ophthal.; May 1985; vol. 103:712/717.
Molteno et al. "Long tube implants in the management of glaucoma" South African Medical Journal, Jun. 26 1976;50(27):1062/6.
Molteno et al. "The Vicryl tie technique for inserting a draining implant in the treatment of secondary glaucoma. " Australian and New Zealand Journal of Ophthalmology 1986; 14: 343/354.
Moses RA "Detachment of ciliary body/anatomical and physical considerations" Investigative Ophthalmology & Visual Science, Assoc. For Research in Vision and Ophthalmology, US, vol. 4, No. 5, Oct. 1, 1965.
Nesterov, AP, et al., "Surgical stimulation of the uveoscleral outflow. Experimental studies on enucleated human eyes" Acta Opthalmol (Copenh) June; 57(3):409/17 (1979).
Nguyen et al., "Complications of Baerveldt Glaucoma Drainage Implants" Arch Ophthal.; May 1998; vol. 116:571/575.
O'Brien et al. "Cyclodialysis" Arch Ophthal. 1949;42(5):606/619.
Odrich. "The New Technique During Complex Tube-Shunt Implantation". J. Glaucoma. vol. 9 No. 3 (2000):205-280.
Olsen, Timothy W., et al., Cannulation of the Suprachoroidal Space: A Novel Drug Delivery Methodology to the Posterior Segment, American Journal of Ophthalmology, vol. 142, No. 5, Nov. 2006, pp. 777-787.e2.
Ozdamar, A., et al., "Suprachoroidal seton implantation in refractory glaucoma: a novel surgical technique" J. Glaucoma Aug. 2003; 12(4):354/9.
Pinnas, G. et al. "Cyclodialysis with teflon tube implants" Am J. Ophthalmol 1969 Nove; 68(5):879/883.
Portney GL, "Silicone elastomer implantation cyclodialysis." Arch Ophthalmol 1973; 89: 10-12.
Pruett et al., "The Fishmouth Phenomenon/II. Wedge Scleral Buckling" Arch Ophthal.; Oct. 1977; vol. 95:1782/1787.
Qadeer "Acrylic Gonio/Subconjunctival Plates in Glaucoma Surgery" Br J Ophthalmol. Jun. 1954; 38(6): 353-356.
Quigley HA, Vitale S. Models of open/angle glaucoma prevalence and incidence in the United States. Invest Ophthalmol Vis Sci 1997; 38:83/91.
Richards et al. "Artificial Drainage Tubes for Glaucoma" Am J Ophth 60:1965,405/408.
Ritch R, Shields MB, Krupin T. The Glaucomas. St. Louis: Mosby, 1996; 337 / 343).
Rohen, Johannes W., Anatomy of the Aqueous Outflow Channels, Glaucoma, vol. 1, Chapter 14, pp. 277-296, Edited by J.E. Cairns, Grune & Stratton, Harcourt Brace Jovanovich Publishers, 1986.
Rosenberg, L., et al. "Implants in glaucoma surgery" Chapter 88, The Glaucomas, Ritch et al. Eds. 2nd Ed. Mosby St. Louis 1986; p. 1783/1807.
Row, H., "Operation to control glaucoma: preliminary report"(1934) Arch. Ophthal 12:325.
Rowan, Patrick J., MD, Combined Cyclodialysis and Cataract Surgery, Ophthalmic Surgery and Lasers, Dec. 1998, vol. 29, No. 12, pp. 962-968 (9 pages).
Sampimon "A New Approach to Filtering Glaucoma Surgery" Ophthalmologica (Basel) 151: 1966, 637/644.
Schappert S. Office visits for glaucoma: United States, 1991/92. Advance data from vital and health statistics. vol. 262. Hyattsville, MD: National Center for Health Statistics, 1995.
Schocket, Stanley S. "Investigations of the Reasons for Success and Failure in the Anterior Shunt-To-The-Encircling-Band Procedure in the Treatment of Refractory Glaucoma." *Tr. Am. Ophth. Soc.*vol. LXXXIX. (1986):743-798.
Shaffer RN, Weiss DI. Concerning cyclodialysis and hypotony. Arch Ophthalmol 68: 25, 1962.
SOLX Clinical Literature Handout; Industry Show Feb. 2006; "The SOLX Gold Micro/shunt (GMS) treatment".
Sommer A, Tielsch JM, Katz J, et al. Racial differences in the cause/specific prevalence of blindness in east Baltimore. N Engl J Med 1991;325:1412/7.
Sourdille et al. "Reticulated hyaluronic acid implant in non/perforating trabecular surgery." J Cataract Refract Surg 25: 332-339. (1999):.
Spiegel et al. "Schlemm's Canal Implant: A New Method to Lower Intraocular Pressure in Patients With POAG?" Ophthalmic Surgery and Lasers. vol. 30, No. 6: 492-494. Jun. 1999.
Srinivasan, R., et al., "Microbial contamination of the anterior chamber during phacoemulsification" J. Cataract Refract Surg. 28:2173/6 (2002).
Suguro K, Toris CB, Pederson JE. Uveoscleral outflow following cyclodialysis in the monkey eye using a fluorescent tracer. Invest Ophthalmol Vis Sci 1985: 26, 810.
The Advanced Glaucoma Intervention Study (AGIS): 7. The relationship between control of intraocular pressure and visual field deterioration. The AGIS Investigators. Am J Ophthalmol 2000;130:429/40.
The Glaucoma Laser Trial (GLT) and Glaucoma Laser Trial Follow/up Study: 7. Results. Am J Ophthahnol 1995;120:718/31.
The Glaucoma Laser Trial (GLT). 2. Results of argon laser trabeculoplasty versus topical medicines. The Glaucoma Laser Trial Research Group. Ophthalmology 1990;97:1403/13.
Tielsch JM, Sommer A, Katz J, et al. Racial variations in the prevalence of primary open/angle glaucoma. The Baltimore Eye Survey. JAMA 1991;266:369/74.

(56) References Cited

OTHER PUBLICATIONS

Toris CB. Extravascular albumin concentration of the uvea. Invest Ophthalmol Vis Sci 1990; 31: 43.

Toris et al. "Effect of intraocular pressure on uveoscleral outflow following cyclodialysis in the monkey eye." Investigative Ophthalmology & Visual Science. 26 (1985) 1745-1749.

Toris, C., et al., "Aqueous humor dynamics in the aging human eye" Am J. Ophthalmol., 127:407/12 (1999).

*Transcend Medical Inc.* v. *Glaukos Corporation*, Transcend Medical, Inc.'s Disclosures Pursuant to Default Discovery Rule 4 (d) (United States District Court for the District of Delaware, dated Dec. 6, 2013; case No. C.A. No. 13-830 (MSG) and Certificate of Service, dated Dec. 9, 2013.

Troncosco, U.M., "Cyclodialysis with insertion of metal implant in treatment of glaucoma Preliminary report" Arch. Ophthal. 23:270 (1940).

Troncoso, Manuel U., Tantalum implants for inducing hypotny, Am Journal of Ophthalmology, vol. 32(4):499-508 (1949).

Van Der Veen et al. "The gonioseton, a surgical treatment for chronic glaucoma." Documenta Ophthalmologica Oct. 1990, vol. 75, Issue 3-4, pp. 365-375.

Wagner, Justin A., et al., Characterization of Uveoscleral Outflow in Enucleated Porcine Eyes Perfused under Constant Pressure, Invest Ophthalmol Vis Sci., Published in edited form in Sep. 2004, vol. 45, Issue 9, pp. 3203-3206.

Yablonski, "Trabeculectomy with Internal Tube Shunt: a novel glaucoma surgery" J. Glaucoma 14:91/97 (2005).

Yablonski, M., "Some thoughts on the pressure dependence of uveoscleral flow" Journal of Glaucoma, 12(1):90/92 (2003).

Zhou, J., et al., "A trabecular bypass flow hypothesis" J Glaucoma. 14(1):74/83 (2005).

U.S. Appl. No. 13/865,927, filed Apr. 18, 2013, 2013-0281817.
U.S. Appl. No. 14/071,500, filed Nov. 4, 2013, 2014-0066831.
U.S. Appl. No. 14/078,206, filed Nov. 12, 2013, 2014-0135916.
U.S. Appl. No. 14/140,322, filed Dec. 24, 2013, 2014-0107556.
U.S. Appl. No. 14/163,364, filed Jan. 24, 2014, 2014-0213958.
U.S. Appl. No. 14/254,366, filed Apr. 16, 2014, 2014-0309599.
U.S. Appl. No. 14/260,041, filed Apr. 23, 2014, 2014-0323995.
U.S. Appl. No. 14/283,759, filed May 21, 2014, 2014-0364789.
U.S. Appl. No. 14/610,197, filed Jan. 30, 2015, 2015-0223982.
U.S. Appl. No. 14/706,893, filed May 7, 2015, 2015-0238360.
U.S. Appl. No. 14/804,008, filed Jul. 20, 2015, 2015-0320596.
U.S. Appl. No. 14/987,133, filed Jan. 14, 2016, 2016-0193083.
U.S. Appl. No. 15/005,745, filed Jan. 25, 2016, 2016-0135992.
U.S. Appl. No. 15/268,305, filed Sep. 16, 2016, 2017-0079839.
PCT/US2016/052267, filed Sep. 16, 2016, WO 2017/051247.
U.S. Appl. No. 15/693,920, filed Sep. 1, 2017, 2018-0071143.
U.S. Appl. No. 15/710,618, filed Sep. 20, 2017, 2018-0092775.
U.S. Appl. No. 15/843,703, filed Dec. 15, 2017, 2018-0104103.
U.S. Appl. No. 15/912,040, filed Mar. 5, 2018, 2018-0256397.

\* cited by examiner

OCULAR PRESSURE REGULATION

CROSS-REFERENCE TO RELATED APPLICATIONS

This application is a continuation of co-pending U.S. application Ser. No. 14/199,737, filed Mar. 6, 2014, entitled "OCULAR PRESSURE REGULATION" by Minas Coroneo; now U.S. Pat. No. 9,351,873 which is a continuation of U.S. application Ser. No. 12/905,003, filed Oct. 14, 2010, entitled "OCULAR PRESSURE REGULATION" by Minas Coroneo, now U.S. Pat. No. 8,808,220, issued Aug. 19, 2014; which is a continuation of U.S. application Ser. No. 11/615,642, filed Dec. 22, 2006, entitled "OCULAR PRESSURE REGULATION" by Minas Coroneo, now U.S. Pat. No. 8,128,588, issued Mar. 6, 2012; which is a continuation of U.S. application Ser. No. 10/712,277, filed Nov. 14, 2003, entitled "OCULAR PRESSURE REGULATION" by Minas Coroneo, now U.S. Pat. No. 7,291,125, issued Nov. 6, 2007.

This application also is related to U.S. application Ser. No. 10/579,330, filed Nov. 12, 2004, entitled "OCULAR PRESSURE REGULATION" by Minas Coroneo, now U.S. Pat. No. 8,486,000, issued Jul. 16, 2013; and to U.S. application Ser. No. 11/615,615, Dec. 22, 2006, entitled "OCULAR PRESSURE REGULATION" by Minas Coroneo, now U.S. Pat. No. 7,850,638, issued Dec. 14, 2010; and to U.S. application Ser. No. 12/107,676, filed on Apr. 22, 2008, entitled "OCULAR PRESSURE REGULATION" by Minas Coroneo, now U.S. Pat. No. 7,815,592, issued Oct. 19, 2010.

Where permitted, the subject matter of each of the above noted applications is hereby incorporated by reference in its entirety by reference thereto.

FIELD OF THE INVENTION

This invention is directed to therapeutic methods and devices for the treatment of glaucoma. In particular, this invention is concerned with the use of a shunt or drain for the treatment of glaucoma. In another aspect this invention is concerned with ocular pressure spike shunts and use of the same in ocular surgery.

BACKGROUND OF THE INVENTION

The glaucomas are a common group of blinding conditions usually associated with elevated intraocular pressure. This elevated pressure in the eye may be regarded as a disorder of the drainage system of the eye which gives rise to the glaucomas.

Aqueous humor of the eye ("aqueous") is a flowing liquid fluid (composed of sodium, chloride, bicarb, amino acids, glucose, ascorbic acid, and water) that is actively secreted by the ciliary body and flows out past the iris into the anterior chamber (are between the lens/iris and the cornea). The aqueous drains out through angle formed by the iris and the sclera into a meshwork call the trabeculum, and from there into the canal of Schlemm and then into the episcleral veins. Uveosclera drainage also occurs. Normal intraocular pressure (TOP) of aqueous in anterior chamber is between 10 and 20 mm Hg. Prolonged IOPs of greater than 21 mm Hg are associated with damage to optic nerve fibers.

In some cases of glaucoma the cause can be found: the trabecular meshwork becomes blocked by pigment or membrane. In other cases, blockage is due to a closure of the angle between the iris and the cornea. This angle type of glaucoma is referred to as "angle-closure glaucoma". In the majority of glaucoma cases, however, called "open angle glaucoma", the cause is unknown.

Elevated intraocular pressure results in the death of retinal ganglion cells (which convey retinal information to the brain) resulting in a characteristic pattern of loss of the field of vision, progressing to tunnel vision and blindness if left untreated.

Treatment of glaucoma consists predominantly of methods to lower the intraocular pressure (pharmacological, trabecular meshwork laser and surgery to drain fluid from the eye). More recently protection of the retinal ganglion cells by neuroprotective agents has been attempted.

Although pharmacological treatments of glaucoma have improved, they have important implications for the patient's quality of life, have compliance issues which are important in the elderly (in whom glaucoma is prevalent), expose the patient of glaucoma to side effects, and over a lifetime are costly.

Surgery for glaucoma treatment is usually a trabeculectomy in which a fistula is created to drain fluid from the anterior chamber to the subconjunctival space near the limbus, creating a bulge in the conjunctiva known as a bleb. Frequently scarring occurs and attempts to counter this with antimetabolites such as Mitomycin C have met with some success. In recalcitrant cases, glaucoma implants, drainage, shunt or valve devices have been developed e.g. Molteno (U.S. Pat. No. 4,457,757), Krupin (U.S. Pat. No. 5,454,746) and Baerveldt (U.S. Pat. No. 5,178,604). These suffer from similar problems of scarring (Classen L, Kivela T, Tarkkanen "A Histopathologic and immunohistochemical analysis of the filtration bleb after unsuccessful glaucoma seton implantation" *Am J Ophthalmol*, 1996; 122:205-12) around the external opening of the tube devices in the subconjunctival space—the development of a large number of these devices is testament to the fact that many fail in the longer term. In these devices a drainage tube is located in the anterior chamber and is in fluid communication with the sclera or a surgically created subconjunctival space.

Whereas cataract surgery has been revolutionized in the last two decades, improvements in glaucoma surgery have been slower. Antifibrotic agents have improved the success rate of conventional filtration surgery (trabeculectomy), but with increased bleb leaks, blebitis, endophthalmitis and hypotensive maculopathy. Glaucoma shunts have had limited success in eyes that have "failed" multiple standard procedures. However complications with malpositioned tubes, erosion and strabismus persist. A considerable issue is the lack of reproducibility and predictability in achieving the desired target intraocular pressure (IOP). Final IOP is largely determined by healing which can be unpredictable—in view of vast biological variations, it is impossible to predict which eyes will rapidly scar causing failure and which will fail to heal resulting in prolonged post-operative hypotony. Scarring remains a significant problem in all these external drainage proposals, where aqueous drains into the conjunctiva, or surgical chambers in the sclera.

The introduction of a new class of antiglaucoma drugs, the prostaglandin analogues, has resulted in acknowledgment of the importance of the uveoscleral pathway in drainage of fluid form the eye (Hylton C, Robin A L "Update on prostaglandin analogs" *Curr Opin Ophthalmol*, 2003; 14:65-9). Uveoscleral flow where aqueous humor flows through the interstitium of the ciliary muscle into the suprachoroidal space (a potential space between the choroids and sclera) and out through the sclera into the connective tissue of the orbit may account for 54% of outflow young healthy humans (Toris C B, Yablonski M E, Wang Y L, Camras C B "Aqueous humor dynamics in the aging human eye" *Am J Ophthalmol,* 1999; 127:407-12).

Cyclodialysis, the separation of the ciliary body from the scleral spur and underlying sclera, creates free communication between the anterior chamber and the suprachoroidal space and enhances uveoscleral flow. It has long been known that cyclodialysis can cause a profound reduction of intraocular pressure—initially (Fuchs E. "Detachment of the choroid inadvertently during cataract surgery" [German] *von Graefes Arch Ophthalmol,* 1900; 51:199-224) cyclodialysis was recognized as a complication of cataract surgery. Deliberate creation of a cyclodialysis cleft for treating elevated intraocular pressure in uncontrolled glaucoma was first described as a surgical procedure in 1905 (Heine I. "Cyclodialysis, a new glaucoma operation" [German]) *Dtsch Med Wochenschr,* 1905; 31:824-826). Since such clefts can heal and close spontaneously a number of devices have been used to keep them open, including platinum wire, horse hair, magnesium strips, tantalum foil, Supramid®, gelatin film, Teflon®, silicone and polymethylmethacrylate (Rosenberg L F, Krupin T. "Implants in glaucoma surgery" Chapter 88, *The Glaucomas,* Ritch R, Shields B M, Krupin T Eds. 2$^{nd}$ Edition Mosby St Louis 1986) and Hema (Mehta K R. "The suprachoroidal Hema wedge in glaucoma surgery" American Academy of Ophthalmology meeting 1977, pp 144). However the success rate of such approaches has been low (as low as 15%, Rosenburg & Krupin ibid and Gross R L, Feldman R M, Spaeth G L, et al "Surgical therapy of chronic glaucoma in aphakia and pseudophakia" *Ophthalmology,* 1988; 95:1195-201). Failure was due to uncontrolled low pressure (hypotony) with consequential macular edema, bleeding (hyphema) and inadequate pressure control.

The device and method of a first aspect of this invention takes advantage of the methods used in cataract surgery to develop a minimally invasive glaucoma procedure—thus small, self sealing incisions and materials that are biocompatible and foldable so that they fit through small openings will reduce surgical trauma and time. The controlled draining of aqueous into the suprachoroidal space according to this invention provides some predictability of outcome and overcomes scarring problems that have plagued glaucoma implants in the past.

The most frequent complication following modern cataract surgery with phacoemulsification, requiring specific treatment is elevated intraocular pressure (Cohen V M, Demetria H, Jordan K, Lamb R J, Vivian A J.: First day post-operative review following uncomplicated phacoemulsification" *Eye,* 1998; 12 (Pt 4):634-6, and Dinakaran S, Desai S P, Raj P S. "Is the first post-operative day review necessary following uncomplicated phacoemulsification surgery?" *Eye,* 2000 June; 14 (Pt 3A):364-6). The increase may be marked and typically peaks at 5 to 7 hours before returning to near normal levels in 1 to 3 days (Hildebrand G D, Wickremasinghe S S, Tranos P G, Harris M L, Little B C. "Efficacy of anterior chamber decompression in controlling early intraocular pressure spikes after uneventful phacoemulsification" *J Cataract Refract Surg.,* 2003; 29:1087-92). Such pressure spikes can cause pain and may increase the risk of sight-threatening complications such as retinal vascular occlusion, increases loss of visual field in advanced glaucoma and ischemic optic neuropathy—effects in otherwise healthy eyes are unknown (Hildebrand G D et al, ibid).

A number of prophylactic treatments are used with limited success—these include intracameral carbachol or acetylcholine, topical timolol, dorzolamide, aproclonidine, latanoprost and systemic acetazolamide (see Hildebrand G D et al, ibid). This also exposes the patient to the risk of drug side effects, increased cost and it has been postulated that reducing the flow of aqueous humor post surgery prolongs the residence time of bacteria that frequently (46.3% of cases) contaminate the anterior chamber during surgery (Srinivasan R, Tiroumal S, Kanungo R, Natarajan M K. "Microbial contamination of the anterior chamber during phacoemulsification" *J Cataract Refract Surg,* 2002; 28:2173-6.). This may increase the risk of endophthalmitis one of the most devastating sequelae of intraocular surgery, since the bacteria are not being "flushed out" of the eye by the normal production of aqueous humour, the secretion of which has been suppressed by the drugs. Another technique is to decompress the anterior chamber by applying pressure to the posterior lip of the paracentesis wound at the appropriate time. This requires surveillance and could increase the risk of infection. Another aspect of this invention hereinafter described overcomes these problems.

SUMMARY OF THE INVENTION

According to the present invention there is provided a flexible ocular device for implantation into the eye formed of a biocompatible elastomeric material, foldable to a diameter of 1.5 mm or less, comprising a fluid drainage tube having at one end a foldable plate adapted to locate the device on the inner surface of the sclera in a suprachoroidal space formed by cyclodialysis, said drainage tube opening onto the disc at one end and opening to the anterior chamber when implanted into the eye at its other end, so as to provide aqueous pressure regulation.

Preferably the fluid drainage tube has a diameter selected to provide predetermined resistance to aqueous humor flow, for example a pressure of 10 mm Hg or less. Alternatively said tube contains a valve so as to regulate pressure of the aqueous chamber at a predetermined level, for example, at no less than 10 mm Hg.

In accordance with another embodiment of this invention there is provided a method for treating glaucoma which comprises:

providing a flexible ocular device formed of a biocompatible elastomeric material foldable to a diameter of 1.5 mm or less, comprising a fluid drainage tube having at one end a foldable plate adapted to locate the device on the inner surface of the sclera and at its other end being open so as to allow fluid communication through said tube;

forming a small self-sealing incision at the juncture of the cornea and sclera of the eye opening into the anterior chamber;

filling the anterior chamber with a viscoelastic substance;

introducing the foldable ocular device into a suprachoroidal space formed by cyclodialysis via a hollow cannula, wherein said plate locates the device on the inner surface of the sclera in the suprachoroidal space, and said drainage tube is located in the anterior chamber of the eye so as to provide aqueous humor pressure regulation; and thereafter removing said cannula and viscoelastic material from the eye.

In another aspect there is provided an ocular pressure spike shunt for insertion into an ocular paracentesis incision port following ocular surgery, comprising a flexible fluid transfer tube formed of biocompatible material, preferably biocompatible elastomeric material, so as to allow paracentesis incision closure around said tube, having an inner end and an outer end, a tubular lumen disposed between said inner end and said outer end to allow fluid communication through said tube, said lumen containing a valve for controlling pressure in the eye following ocular surgery, which valve opens permitting fluid flow through said tube when a predetermined pressure is exceeded, said shunt being configured such that on insertion into a paracentesis port said outer end is substantially flush with the surface of the cornea, and said inner end opens into the anterior chamber of the eye.

In another aspect there is provided a method for preventing ocular pressure spikes following ocular surgery wherein a paracentesis incision port is formed in the eye during said surgery, comprising introducing an ocular pressure spike shunt into said paracentesis port at the conclusion of ocular surgery, said shunt comprising a flexible fluid transfer tube formed of biocompatible material, preferably biocompatible elastomeric material, so as to allow paracentesis incision closure around said tube, having an inner end and an outer end, a tubular lumen disposed between said inner end and said outer end to allow fluid communication through said tube, said lumen containing a valve for controlling pressure in the eye following ocular surgery, which valve opens permitting fluid flow through said tube when a predetermined pressure is exceeded, said shunt being configured such that on insertion into a paracentesis port said outer end is substantially flush with the surface of the cornea, and said inner end protrudes into the anterior chamber of the eye.

DETAILED DESCRIPTION OF THE PREFERRED EMBODIMENTS OF THE INVENTION

The ocular device according to the present invention is implanted in a patient's eye using minimally invasive surgery techniques, adopted from modern cataract surgery.

Figure 1:
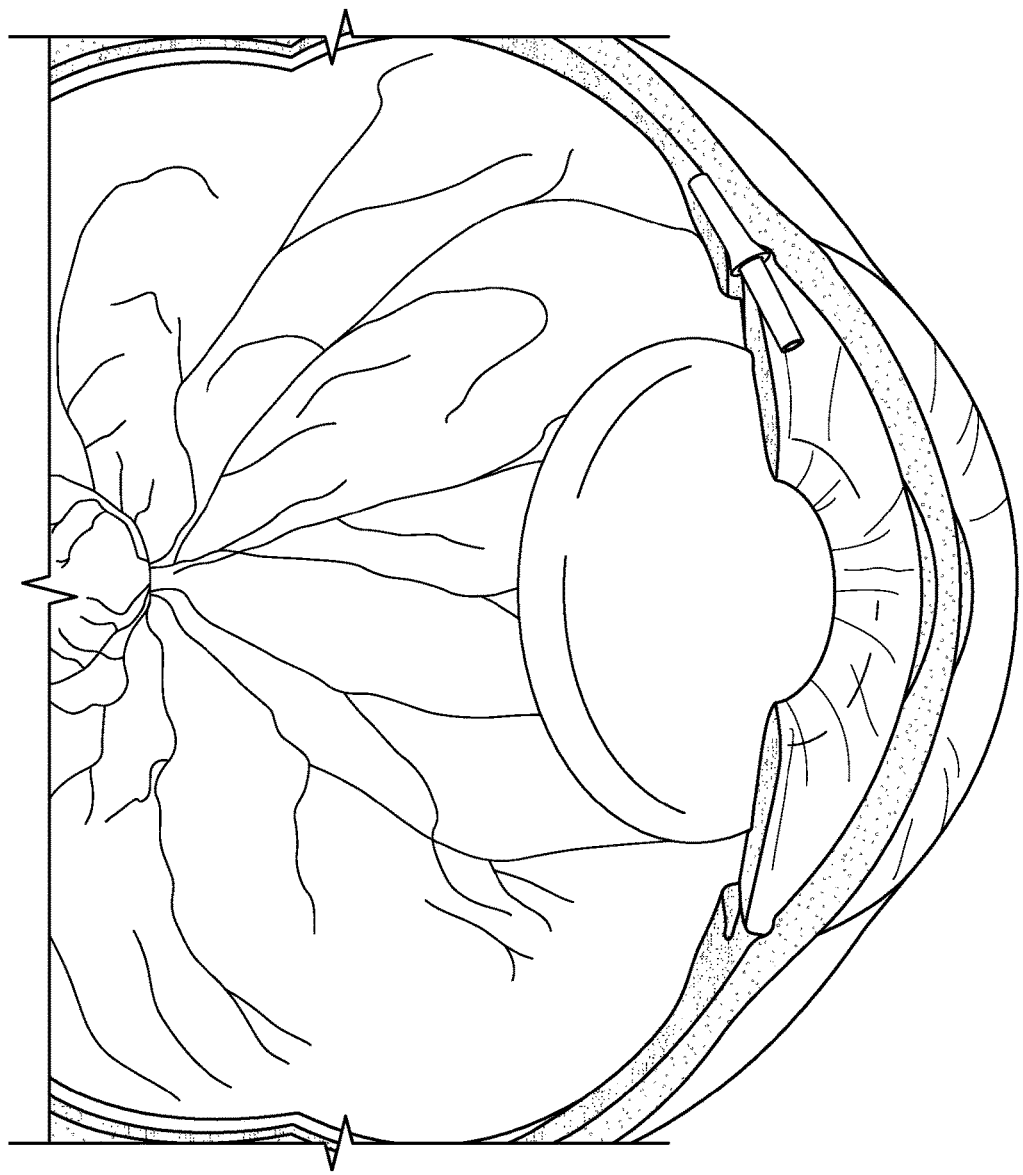
FIG. 1 shows a diagrammatic representation of a side sectional view of suprachoroidal shunt insertion using an injector.

The ocular device is formed from a biocompatible elastomeric material. Preferably, the device is made of soft surgical grade polymeric material, such as silicon or acrylic material such that the device is foldable and may be rolled up for insertion via a cannula. FIG. 1 shows a proximal end of a cannula forming a cyclodialysis. The folded device may be introduced via such a cannula The elastomeric material is selected to be sufficiently soft that it does not erode delicate underlying choroid material when inserted into the eye. Such material and ocular lenses formed therefrom are well known and used in cataract surgery.

Figure 2:
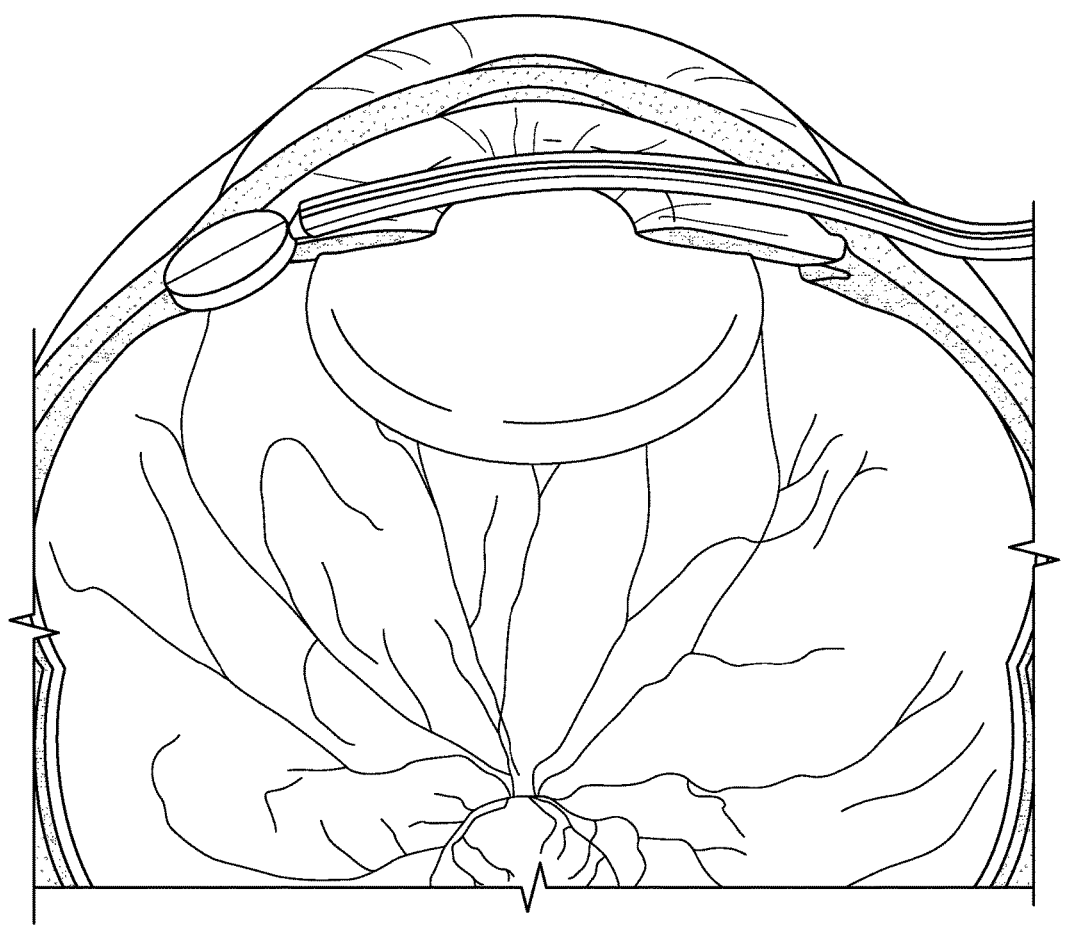
FIG. 2 shows a diagrammatic representation of a side sectional view of an eye showing the unfolded plate portion of the device and a cannula introducing said device across the anterior chamber at 180° to the site of insertion.

Sutures are not required to hold the device in place once surgically introduced into the eye, as the foldable plate is adapted to locate the device on the inner surface of the sclera in a suprachoroidal space formed by cyclodialysis (FIG. 2). Preferably, the plate is of a disc-like shape which matches the curvature of the eye once unfolded. FIG. 2 depicts an unfolded disc (connected tube not shown) after cannula introduction across the anterior chamber (transcameral). Alternatively, any plate-like configuration which locates the device on the inner surface of the sclera in the suprachoroidal space may be used, such as for example a rectangular foldable plate. Preferably the plate diameter is from 0.05 to 6 mm, and preferably the place thickness is from 12.5 µm to 250 µm. The fluid drainage tube of the ocular device is preferably integral with the plate, and is attached at one end to the plate, preferably at the periphery of the plate. Alternatively, the tube may be microwelded or otherwise fixed to the plate. Fabrication techniques well known in production of intraocular foldable lenses are preferably used in this invention. The tube has a hollow lumen, and is preferably of a length from about 1 mm to 4 mm. Preferred diameters of the tubing comprise an outer diameter of 400-1000 µm, and preferably the inner diameter is from 50 to 500 µm.

The diameter of the tube may be selected so as to provide a resistance to aqueous humor flow of predetermined pressure, preferably being a pressure less than 10 mm Hg. This enables the pressure of the aqueous to be regulated in a controlled manner, providing relief from excess ocular pressure associated with glaucoma, with avoidance of hypotony (uncontrolled low pressure). Alternatively, the tube may contain a valve, for example disposed at the end of the tube opening onto the disc so as to regulate ocular pressure at a predetermined level. Preferably, the valve prevents aqueous flow through the tube at a pressure of less than 10 mm Hg. Examples of valves which may be used include a slit valve. The drainage stops altogether if the pressure drops to a predetermined threshold level controlled by the valve.

The flexible foldable nature of the device according to the present invention enables well established techniques used in cataract surgery to be employed in the treatment of glaucoma. The device according to the present invention may be folded into a cannula and introduced for location into the eye.

Intraocular surgery techniques allow a paracentesis (opening onto the anterior chamber from without at the juncture of the cornea and sclera—the limbus) to be performed and the anterior chamber filled with viscoelastic substance. A cyclodialysis instrument is introduced via the paracentesis, with the paracentesis preferably being carried out 180° from the insertion site. A cyclodialysis is carried out, for example by advancing an instrument tip into the angle between the ciliary body and sclera so as to create a cyclodialysis. This is preferably carried out with direct visualisation via gonioscopy lens viewed through an operating microscope. A surgical gonioscopy lens is preferably placed on the cornea while the cyclodialysis is carried out.

The rolled up ocular device is introduced through a cannula, for example using an introducer such as used in cataract surgery or other ocular surgery, from which the device can be detached by pressing a plunger into the introducer when the device has been inserted into the suprachoroidal space created by the cyclodialysis. The tubing of the device is positioned into the interior chamber, and the plate unfolds in the suprachoroidal space to locate the device in the eye. Because of its size, the device cannot fall through the opening through which it was introduced into the suprachoroidal space by the cyclodialysis. The plate therefore keeps the tube in the appropriate position in the anterior chamber allowing controlled aqueous drainage and providing an effective treatment for elevated ocular pressure.

Figure 3:
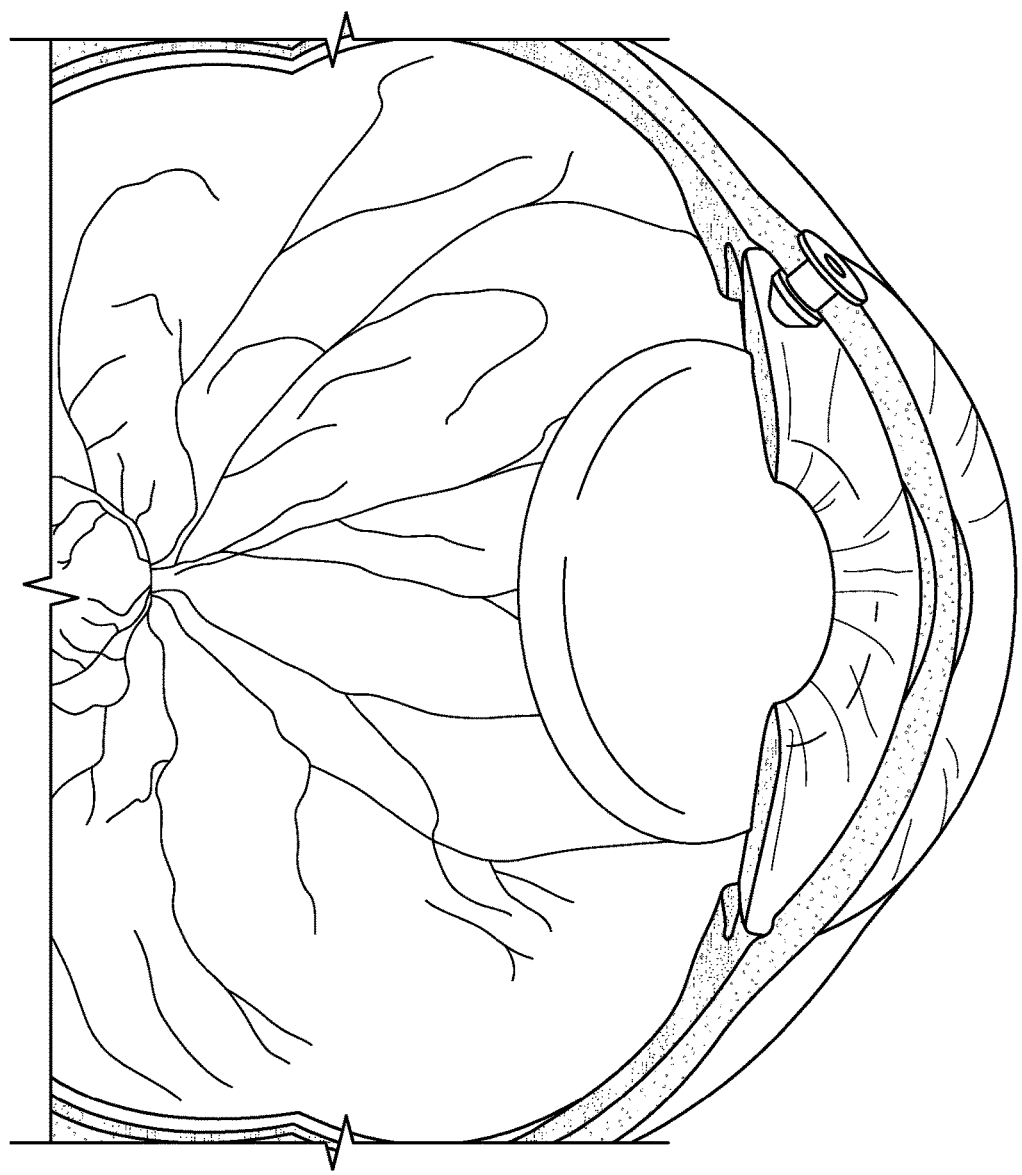
FIG. 3 shows a diagrammatic representation of an eye containing a pressure spike shunt inserted into a paracentesis port.
Figure 4:
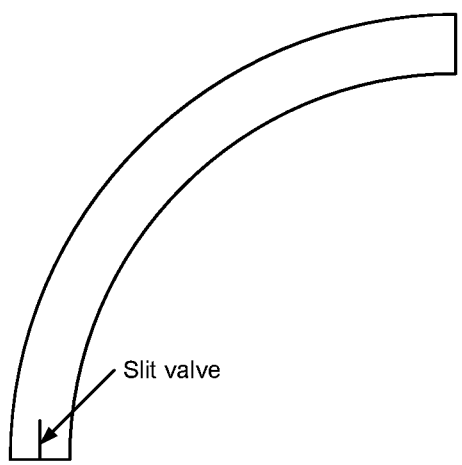
FIG. 4 shows a perspective view of another embodiment of an ocular device described herein.

The pressure spike shunt is designed to fit snugly in a paracentesis port that is routinely made during cataract or other ocular surgery. The tubing will not distort the port and there will be no leakage around the port. The outer end of the tube will sit flush on the surface of the cornea—the inner aspect of the tube will preferably just protrude into the anterior chamber—tube length will generally be 1-2 mm and tube diameter is preferably from 0.4-1.2 mm. The tube will contain the same valvular device as contained in the ocular device described above and will open when the intraocular pressure exceeds a predetermined level, preferably 10 mm Hg. At normal ocular pressure the valve will be closed, closing said tube to any fluid communication. FIG. 3 shows a shunt located in a paracentesis port. In most cases the shunt will be removed and discarded at the first post-operative dressing.

The shunt may be inserted into a paracentesis port, or one or more ports, using, for example, a punctum plug inserting instrument such as described in U.S. Pat. No. 5,741,292.

This invention will now be described with reference to the following examples.

Example 1

Fresh whole porcine eyes were taken and mounted in a temperature controlled)(37°) perfusion chamber. The eyes were perfused with Balanced Salt Solution via a 30 gauge needle inserted via a paracentesis into the anterior chamber. A peristaltic pump was used at a flow rate of 2 µl/min. Intraocular pressure was continuously monitored via a second paracentesis.

Typically intraocular pressures stabilized at 10-15 mm Hg and fell with time (the "washout effect", as glycosan aminoglycans are washed out of the trabecular meshwork with time). Creation of a cyclodialysis (initially with a small spatula, then viscoelastic injection to enlarge the area of detachment of the ciliary body from the sclera) with or without insertion of the device in the cyclodialysis cleft (silicone tubing, length 3 mm, external diameter—1 mm, plate diameter 3 mm) resulted in lower intraocular pressures (below 10 mm Hg) on reperfusion at the same perfusion rate as control eyes.

Example 2

Adequate anesthesia is provided to the eye of a glaucoma patient prepared for intraocular surgery. A paracentesis (opening into anterior chamber from without at the junction of the cornea and sclera—the limbus) is performed and the anterior chamber is filled with a viscoelastic substance. A surgical gonioscopy lens is placed on the cornea (or anterior segment endoscope is used) and a cyclodialysis instrument is introduced via the paracentesis—the paracentesis is carried out 180° away from the planned implant insertion site. The cyclodialysis instrument tip is advanced into the angle and pushed into the space between the ciliary body and sclera creating a cyclodialysis—this is carried out with direct visualization via the gonioscopy lens viewed through an operating microscope. In order to minimize bleeding, the area in the angle (anterior ciliary body face and overlying trabecular meshwork) can be lasered either preoperatively or at the time of surgery to ablate surface blood vessels).

Through an opening at the tip of the cyclodialysis instrument viscoelastic is inserted to further create a space in the suprachoroidal space. The implant is then introduced—the device is rolled up in the same manner as an ultrathin intraocular lens. The ocular device is attached to an introducer from which it is detached by pushing a plunger in the introducer when the implant is inserted into the suprachoroidal space created by the cyclodialysis instrument and viscoelastic. The tubing is then positioned into the anterior chamber and may be cut to size. The plate unfolds in the suprachoroidal space and because of its size cannot fall through the opening through which it was introduced into the suprachoroidal space. The plate therefore keeps the tube in an appropriate position. The valve is then flushed (with a cannula inserted via the paracentesis) via the tube opening in the anterior chamber. Viscoelastic is then removed from the anterior chamber and antibiotics, steroids and a dressing applied to the eye.

Example 3

Fresh whole porcine eyes were taken and mounted in a temperature-controlled (37°) perfusion chamber as in Example 1. The eyes were perfused with Balanced Salt Solution via a 30 gauge needle inserted via a paracentesis into the anterior chamber. A peristaltic pump was used at a flow rate of 2 µl/min. Intraocular pressure was continuously monitored via a second paracentesis.

Typically intraocular pressures stabilized at 10-15 mm Hg and fell with time (the "washout effect, as glycoaminoglycans are washed out of the trabecular meshwork with time). Silicone tubing (length 3 mm, external diameter 1 mm) was introduced into one paracentesis port. One end of the port (outer end) was flush with the cornea and the inner end of the port extended slightly into the anterior chamber. Intraocular pressure did not exceed 10 mm Hg.

What is claimed is:

1. A method of treating an ocular disorder, comprising:
providing an implant having a distal end, a proximal end and a longitudinal, internal lumen extending through the ophthalmic implant and wherein the distal end of the implant includes a round, foldable plate adapted to locate the device on the inner surface of a sclera of the eye;
rolling up at least a portion of the implant to form a rolled up implant;
introducing the rolled up implant into a cannula;
forming an opening in a cornea into the anterior chamber of an eye;
filling the anterior chamber with a viscoelastic substance;
introducing the implant via the cannula through the opening, wherein at least the proximal end of the implant passes through the anterior chamber;
forming previously non-existing space in the eye by separating at least a portion of the ciliary body from at least a portion of the sclera from within the anterior chamber to form the space;
implanting the distal end of the implant in communication with the space; and
permitting aqueous humour to flow through the internal lumen from the anterior chamber towards the space.

2. A method as in claim 1, wherein the implant comprises a tube.

3. A method as in claim 1, wherein the space comprises at least a portion of the suprachoroidal space.

4. A method as in claim 1, wherein forming a previously non-existing space in the eye comprises performing a cyclodialysis.

5. A method as in claim 4, further comprising inserting viscoelastic to further form the space.

6. A method as in claim 5, wherein inserting the viscoelastic comprises inserting viscoelastic through an attachment between the ciliary body and the sclera.

7. A method as in claim 6, wherein inserting the viscoelastic comprises enlarging an area of detachment of the ciliary body from the sclera.

8. A method as in claim 7, wherein the space extends into the suprachoroidal space.

9. A method as in claim 1, wherein the proximal end of the implant remains in fluid communication with the anterior chamber.

10. A method as in claim 1, wherein introducing through the opening an ophthalmic implant comprises introducing the entire ophthalmic implant into the anterior chamber of the eye.

11. A method as in claim 10, wherein introducing the entire ophthalmic implant into the anterior chamber of the eye comprises passing the distal end and the proximal end of the ophthalmic implant through the cornea.

12. A method as in claim 1, wherein introducing through the incision an ophthalmic implant comprises placing the ophthalmic implant in the eye after forming the space.

13. A method as in claim 1, wherein forming an opening comprises creating a self-sealing incision in the cornea 180 degrees away from a planned insertion site of the ophthalmic implant in the eye.

14. A method as in claim 1, wherein the incision is formed in the limbus of the cornea.

15. A method as in claim 1, further comprising injecting a viscoelastic substance into the anterior chamber of the eye prior to introducing the ophthalmic implant through the opening.

16. A method as in claim 1, wherein aqueous pressure of the eye is maintained at a pressure of not less than 10 mmHg.

\* \* \* \* \*